United States Patent [19]

Hearn et al.

[11] Patent Number: 5,629,451
[45] Date of Patent: May 13, 1997

[54] REDUCTION OF NITRILE CONTAMINANTS BY SELECTIVE HYDROGENATION

[75] Inventors: Dennis Hearn; Kyte H. Terhune, both of Houston, Tex.

[73] Assignee: Chemical Research & Licensing Company, Pasadena, Tex.

[21] Appl. No.: 268,811

[22] Filed: Jun. 30, 1994

[51] Int. Cl.$^6$ .................................................. C07C 209/48
[52] U.S. Cl. ........................ 564/490; 564/491; 564/492; 564/493
[58] Field of Search ............................. 564/490; 210/757

[56] References Cited

U.S. PATENT DOCUMENTS

| | | | |
|---|---|---|---|
| 2,287,219 | 6/1942 | Young et al. | 260/583 |
| 2,449,036 | 9/1948 | Grunfeld | 260/583 |
| 3,186,935 | 6/1965 | Jaell | 208/59 |
| 3,253,040 | 5/1966 | Potter et al. | 260/584 |
| 3,372,195 | 3/1968 | Little et al. | 260/570.7 |
| 3,565,975 | 2/1971 | Mirviss et al. | 260/583 |
| 3,699,036 | 10/1972 | Hass et al. | 208/111 |
| 3,821,305 | 6/1974 | Bartelini | 260/583 |
| 3,998,881 | 12/1976 | Butte, Jr. et al. | 260/563 R |
| 4,166,805 | 9/1979 | Jowett | 252/430 |
| 4,186,146 | 1/1980 | Butte, Jr. et al. | 260/570.5 P |
| 4,222,961 | 9/1980 | Butte, Jr. et al. | 260/563 D |
| 4,235,821 | 11/1980 | Butte, Jr. et al. | 564/491 |
| 4,254,059 | 3/1981 | Grey et al. | 464/492 |
| 4,561,969 | 12/1985 | Janoski et al. | 208/262 |
| 4,739,120 | 4/1988 | Zuckermann | 564/381 |
| 4,886,594 | 12/1989 | Miller | 208/210 |
| 5,009,771 | 4/1991 | Clark et al. | 208/216 PP |
| 5,075,506 | 12/1991 | Zimmerman | 564/490 |
| 5,084,259 | 1/1992 | Satek | 423/277 |
| 5,100,855 | 3/1992 | Clark et al. | 502/211 |
| 5,120,881 | 6/1992 | Rosenfeld et al. | 568/697 |
| 5,147,526 | 9/1992 | Kukes et al. | 208/111 |
| 5,151,172 | 9/1992 | Kukes et al. | 208/144 |
| 5,271,835 | 12/1993 | Gorawara et al. | 208/228 |
| 5,321,163 | 6/1994 | Hickey et al. | 568/55 |

*Primary Examiner*—Brian M. Burn
*Attorney, Agent, or Firm*—Kenneth H. Johnson

[57] ABSTRACT

A process for selectively reducing nitrile contaminants in fluids such as water, methanol or hydrocarbon streams containing mono olefins and which contain minor amounts of contaminants comprising nitriles in the presence of hydrogen and a supported cobalt catalyst. In the olefin stream the nitrile contaminants are substantially reduced without substantial reduction of the mono olefins.

16 Claims, No Drawings

REDUCTION OF NITRILE CONTAMINANTS BY SELECTIVE HYDROGENATION

BACKGROUND OF THE INVENTION

1. Field of the Invention

The present invention relates to the selective hydrogenation of contaminants contained in a light refinery stream.

2. Related Information

Dienes and nitriles are known catalyst poisons in processes using acid catalysts. Many important processes in the petroleum industry require acid catalysts. The production of gasoline octane enhancers such as methyl tertiary butyl ether (MTBE) or tertiary amyl methyl ether (TAME) or catalyzed alkylation processes require acid catalysts.

Mixed refinery streams often contain a broad spectrum of olefinic compounds. This is especially true of products from either catalytic cracking or thermal cracking processes. These olefinic compounds comprise ethylene, acetylene, propylene, propadiene, methylacetylene, butenes, butadiene, etc. Many of these compounds are valuable, especially as feed stocks for chemical products. Ethylene, especially is recovered. Additionally, propylene and the butenes are valuable. However, the olefins having more than one double bond and the acetylenic compounds (having a triple bond) have lesser uses and are detrimental to many of the chemical processes in which the single double bond compounds are used, for example polymerization.

Refinery streams are usually separated by fractional distillation, and because they often contain compounds that are very close in boiling points, such separations are not precise. A $C_5$ stream, for instance, may contain $C_4$'s and up to $C_8$'s. These components may be saturated (alkanes), unsaturated (mono-olefins), or poly-unsaturated (diolefins). Additionally, the components may be any or all of the various isomers of the individual compounds.

Several of the minor components (diolefins) in the feed will react slowly with oxygen during storage to produce "gum" and other undesirable materials. However, these components also react very rapidly in the TAME process to form a yellow, foul smelling gummy material. Thus it is seen to be desirable to remove these components whether the "light naphtha" cut is to be used only for gasoline blending by itself or as feed to a TAME process.

Diene contaminants can be removed by selective hydrogenation in the presence of olefins. The most recommended catalyst being palladium on a support, sometimes with promoters.

Hydrogenation is the reaction of hydrogen with a carbon-carbon multiple bond to "saturate" the compound. This reaction has long been known and is usually done at super-atmospheric pressures and moderate temperatures using an excess of hydrogen over a metal catalyst. Among the metals known to catalyze the hydrogenation reaction are platinum, rhodium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", Hydrocarbon Processing, March 1985, presents an overview of various uses of hydrogenation catalysts, including selective hydrogenation, utilizing a proprietary bimetallic hydrogenation catalyst.

The known method of removal of nitriles from hydrocarbon feeds involves a water wash of the hydrocarbon feed. This requires a number of stages, depending on the relative solubility of the nitrile in water versus hydrocarbon. These additional stages provide additional production costs. It is particularly difficult to remove propionitrile by water wash. The additional stages required for water washing increase complexity and production costs. Although there is a substantial body of art relating to the hydrogenation of nitriles to produce amines or other amino compounds, there is no suggestion as to the fate of olefinic compounds during those processes.

U.S. Pat. No. 2,449,036 teaches the hydrogenation of nitriles to primary amines using nickel or cobalt catalysts providing the reduction is in the presence of a strong aqueous basic solution in ethyl alcohol.

U.S. Pat. No. 3,565,957 discloses the reaction of nitrilotriacetonitrile with hydrogen and a large amount of ammonia in the presence of a catalyst, chosen from a group consisting of nickel, cobalt, and rhodium.

U.S. Pat. No. 4,186,146 discloses the hydrogenation of aromatic nitriles to the corresponding aminomethylbenzene derivatives in a solvent system containing water, ammonia, and water miscible ether solvents using a cobalt or nickel catalyst.

U.S. Pat. No. 4,235,821 discloses the hydrogenation of aliphatic nitriles in a solvent system of water, ammonia, and water miscible ethers using a ruthenium catalyst.

U.S. Pat. No. 4,739,120 teaches the hydrogenation of an organic nitrile group to a primary aminomethyl group in the presence of a rhodium catalyst, a basic substance, and a two-phase solvent system comprising an immiscible organic solvent and water.

U.S. Pat. No. 5,075,506 describes a method for producing secondary amines from fatty nitriles, with ammonia and hydrogen over a cobalt catalyst promoted with zirconium. The catalyst may be supported on kieselguhr or other support. A second stage using the same catalyst but without ammonia, may be used to increase the proportion of secondary amines.

It is an advantage of the present hydrogenation process to selectively hydrogenate contaminants with little if any saturation of the olefins. The absence of hydrogenation of olefins is an unexpected benefit, since cobalt may used as a hydrogenation catalyst for olefins. A particular feature of the present process is that nitriles are hydrogenated to amines, which can be removed easily by water wash, when compared to nitriles, due to fact that the low molecular wt. amines are very soluble in water.

SUMMARY OF THE INVENTION

Briefly, the present invention is the removal of minor amounts of nitrile contaminants from a fluid material by treatment with hydrogen in the presence of a cobalt catalyst.

In one embodiment the present invention is a process for the treatment of olefin containing hydrocarbon streams comprises feeding a light naphtha cut containing mono olefins and minor amounts of contaminants comprising nitriles in the presence of hydrogen and a cobalt catalyst to reduce the contaminants without substantial reduction of the mono olefins. In a further embodiment of the present invention the hydrogenated stream is water washed to remove the amine products of the nitrile hydrogenation.

In another embodiment nitrile contaminants are removed from streams comprising methanol, water and particularly methanol admixed with water.

DETAILED DESCRIPTION AND PREFERRED EMBODIMENTS

Unexpectedly the nitrile contaminant is selectively and substantially removed, while the olefin concentration is substantially unchanged. The nitriles as contaminants are usually present in amounts of about 1 to 5000 ppm which can be substantially reduced or essentially eliminated by the present process.

The catalyst comprise a supported cobalt hydrogenation-dehydrogenation catalyst, such as cobalt oxide or cobalt metal which may comprise from about 1 to 70% of the catalyst. A zirconium promoter may be present as a compound, such as zirconium oxide. The cobalt comprises 30 to 70 wt %, preferably about 40 to 60 wt % of the catalyst. The zirconium comprises about 1 to 5 wt. %, preferably about 2 to 3 wt. % of the catalyst. The supports include alumina, silica, titania, kieselguhr (also called diatomaceous earth, diatomite and infusorial) and the like.

The reaction is preferably carried out at mild temperatures and elevated pressures. The process may generally operate at a temperature in the range of from about 30° to 200° C., more preferably about 60° to 80° C. The pressure may range from about 50 to 5000 psig, preferably from about 200 to 300 psig. The hydrogen is maintained at an excess of that utilized in the process. The rate of hydrogen addition is such as to maintain an excess of hydrogen in the process. The residence time may be expressed as the liquid hourly space velocity (LHSV) which may be in the range of 1–12.

The reaction may be carried out in any suitable reactor, including a fixed bed straight pass reactor, positioned horizontally or vertically, with an up or down flow. A catalytic distillation reactor may also be used.

Suitable feeds for the present process are light refinery streams generally comprising predominately hydrocarbons having up to 9 carbon atoms, e.g., $C_3$ to $C_8$ cuts, usually 4 to 8 linear carbon atoms, including both alkane and alkenes with the impurities noted above. A preferred feed is a $C_5$ cut. The olefins may comprise from about 5 to 95% of the hydrocarbon stream, but generally comprises about 10 to 60%.

The $C_5$'s in the feed are contained in a single "light naphtha" cut which contains everything from $C_5$'s through $C_8$'s and higher. This mixture can easily contain 150 to 200 components and thus identification and separation of the products are difficult.

The diene contaminants may comprise several percent of the feed and may require prior or subsequent treatment to reduce them to very low levels. Dienes may be detrimental to the catalyst and are preferably removed before the present process is applied to a feed. For a similar reason mercaptans and other sulfur compounds are preferably removed before carrying out the present process. However, the nitriles are usually present in only a few parts per million, e.g. up to 100 parts per million and their removal is almost complete, or at least to levels which substantially inhibit the poisoning of resin type catalysts.

Apparatus and General Process

The data that are the subject of this investigation were obtained from an insulated and thermosttated 2'×⅜" i.d. (30 ml. catalyst capacity) copper tube plug-flow reactor. Reaction temperature control was maintained by a steam jacket held at 610.54 torr vacuum (2.89 psia., 149.46 torr) for 140° F. reactions, 576.62 torr (3.72 psia., 192.37 torr) for 150° reactions, and 514.87 torr (4.74 psia., 245.13 torr) for 160° F. reactions. (Matheson Gas Products Model 3491 Vacuum Regulator, Precision Scientific, Inc. Vacuum Pump, Model 31 D-25; 0.88L/min. pumping speed). Temperatures were attained utilizing a bayonet reboiler (Gaumer Co. Model 1P1N5RI, 1", 750 W, 120 VAC Stainless Steel Screw Plug Heater) immersed in the steam jacket water well. Thermostatic conditions were maintained by variable transformer (Staco Type 3 PN1010, 120 VAC) control. An Omega Engineering thermocouple thermometer (Model DP41-TC-A-S2) was used to monitor temperature from two regions: one auxiliary bead-type thermocouple (K-type) strapped onto the steam jacket at the reactor exit (steam jacket front) and one grounded (Omega Engineering Model KQIN-18; ⅛", K-type thermocouple) immersed into the water well at the reactor entrance (steam jacket reflux) and in contact with the steam. The reactor tube was operated "down-flow".

Mixed gas-liquid phase products were maintained in the liquid state by collection in a sample cylinder that was filled from the bottom to top through a tube inserted at the cylinder top and extending to the bottom of the cylinder. Samples were removed into evacuated sample cylinders from the bottom of the loop collection cylinder. A back-pressure regulator (Go, Inc. Model P/N102765) was placed at the exit of the collection system with a cracking pressure of about 150 psig.

Data were tabulated in the form of gas chromatographic integrations (Perkin-Elmer Model 8400 Capillary Column G.C. with a Supelco Separation Technologies Petrocol DH150 150 meter capillary column) and standardized weight percentages from the appropriate response factors. Temperature programming was reemployed as follows: isothermal at 0° C. for 24 min., followed by a 10° C./min. ramp rate to 250° C. where it was held for 24 min. Gas/liquid sample injections onto the GC column were made via a 1μL. loop sample valve connected directly to the injector port.

Additional items include three metering pumps that were used to control the flow of reactants into the reactor tube. Two pumps were used separately and also in conjunction to select a wide range of liquid hourly space (volume flow) velocities (Milton-Roy LDC Division Model 2369-89; Duplex; max. 920 mL./hr. flowrate, Milton-Roy LDC Division Model 396-31 Simplex; 160 ml./hr. max. flowrate). A separate pump was used to pump different reactants, i.e., pure methanol, into the same reactor tube (Eldex Laboratories Model A-60-VS fitted with both motor speed and plunger stroke controls; 180 ml/hr. max. flow).

Feed tank pressures were maintained at about 50–75 psig, well below the pressure in the reactor tube and connecting ⅛" stainless steel tubing and fittings, in order to permit efficient differential pressure pump operation. Reactor system pressures were maintained by a back-pressure regulator (Mity-Mite Model S-91LW, 25–400 psig). Approximately 200–220 psig $N_2$ (gauge: 0–400 psig) was applied at the back-pressure regulator (the reactor exit). There was no observable pressure gradient over the length of the reactor tube. Additionally, a metering pump (Eldex Laboratories, Inc. Model VS-60; 0.05–3.0 mL/hr., controlled both by variable motor speed and manual micrometer-controlled piston stroke) was employed to add methanol to the TAME feed material for catalyst regeneration (see below). Hydrogen flow rate, for the hydrodenitrogenation reaction, was controlled by a gas flow controller (Matheson Gas Products Flowmeter/Controller Model 8270; 0–500 sccm; calibrated for nitrogen gas). Initial reactions were typically carried out under one of two hydrogen flow rates, 100 and 200 sccm, and at one of two temperatures, 125° F. and 212° F. These reactions were accomplished by heating the reactor tube to the reaction temperature, setting the hydrogen flow rate, and then pumping hydrocarbon feed into the reactor tube.

Catalyst

Each catalyst sample was pretreated by outgassing in a catalyst surface area apparatus at 250° C. in vacuo ($10^{-5}$ torr) for 18 hours, then the catalyst metal was chemically reduced by exposure to hydrogen at 250° C. for 18 hours (atmospheric pressure; approx. 760 torr). The sample was then allowed to cool to the ambient temperature in vacuo (approx. $10^{-4}$ to $10^{-5}$ torr). A standard volume was evacuated, filled with CO, and the pressure was then recorded. The catalyst was heated to 200° C. in vacuo in order to desorb the chemisorbed CO.

Hydrogen chemisorption was accomplished by exposing the catalyst to hydrogen, then heating to 200° C., and then allowing it to cool to the ambient temperature in vacuo. The standard volume was evacuated and then filled with hydrogen up to atmospheric pressure. The catalyst was then exposed to the hydrogen. The sample volume containing the catalyst and hydrogen was heated to 100° C. and allowed to remain at this temperature for 1 hour. The sample was then allowed to cool to the ambient temperature and the pressure was recorded.

Propionitrile (PN) and acetonitrile (ACN) are the most common contaminants.

EXAMPLE 1

Hydrotreatment for Nitrile Group Reduction PN and ACN Hydrogenation in $C_5$ Naphtha Feedstock Contaminated with High Diolefin Concentrations.

$CH_3\text{---}C\equiv N + 2H_2 \rightarrow CH_3\text{---}CH_2\text{---}NH_2$ $CH_3\text{---}CH_2\text{---}C\equiv N + 2H_2 \rightarrow CH_3\text{---}CH_2\text{---}CH_2\text{---}NH_2$ The reactor is ⅜ inch ×36 inch stainless steel tube. 35 ml of a catalyst cobalt oxide promoted with zirconium oxide supported on kieselguhr (United Catalyst Inc. G67 RS —54% Co/2.6% Zr on kieselguhr oxide) is loaded in the reactor. The reactor is maintained at temperatures between 100° to 250° F. The pressure is maintained at 250 psig. The LHSV is maintained between 3 to 5. Excess hydrogen is maintained throughout the run. The olefin flow line and the reactor product line were analyzed by gas chromatograph. The olefin feed comprised mostly $C_5$ olefins and saturated hydrocarbons with isoprene, acetonitrile, propionitrile and piperylenes as contaminants. The reactor product line analysis showed selective hydrogenation of diene contaminants with little if any saturation of the $C_5$ olefins.

TABLE I provides a summary composition analysis of the olefin feed and reactor product for the run. The principal contaminant isoprene was reduced by 96% only 0.4% of the olefin was lost.

TABLE I

|  | $H_2$ (moles/hr.) | ACN ppm | ACN (moles/hr.) | %-Conv. | PN ppm | PN (moles/hr.) | %-Conv. |
|---|---|---|---|---|---|---|---|
| FEED PRODUCT | — | 4.50 | — | — | 43.3 | — | — |
| #1[a] | .5354 | 2.20 | $8.04 \times 10^{-4}$ | 51.1% | 29.4 | $5.90 \times 10^{-3}$ | 32.1% |
| #2[b] | .5354 | 0.02 | $8.04 \times 10^{-4}$ | 99.5% | 0.17 | $5.90 \times 10^{-3}$ | 99.6% |
| #3 | .5354 | 1.10 | $16.1 \times 10^{-4}$ | 75.6% | 17.4 | $11.8 \times 10^{-3}$ | 59.8% |
| #4 | .2677 | 0.00 | $8.04 \times 10^{-4}$ | 100% | 0.02 | $5.90 \times 10^{-3}$ | 99.9% |
| #5 | .2677 | 0.80 | $16.1 \times 10^{-4}$ | 82.2% | 14.5 | $11.8 \times 10^{-3}$ | 66.5% |
| #6 | .0857 | 3.00 | $8.04 \times 10^{-4}$ | 33.3% | 34.1 | $5.90 \times 10^{-3}$ | 21.2% |
| #7 | .0483 | 0.02 | $8.04 \times 10^{-4}$ | 99.5% | 2.50 | $5.90 \times 10^{-3}$ | 92.2% |
| #8[c] | .5354 | 0.50 | $8.04 \times 10^{-4}$ | 47.0% | 9.00 | $5.90 \times 10^{-3}$ | 79.2% |
| #9[d] | .5354 | 0.40 | $8.04 \times 10^{-4}$ | 88.9% | 7.10 | $5.90 \times 10^{-3}$ | 83.6% |
| #10[e] | .5354 | 0.35 | $10.6 \times 10^{-4}$ | 92.2% | 3.90 | $7.79 \times 10^{-3}$ | 91.0% |
| #11 | .0937 | 0.025 | $10.6 \times 10^{-4}$ | 99.4% | 0.029 | $7.79 \times 10^{-3}$ | 99.9% |
| #12[f] | .0937 | 4.50 | $10.6 \times 10^{-4}$ | 00.0% | 43.3 | $7.79 \times 10^{-3}$ | 0.0% |
| #13[g] | .0937 | 4.50 | $9.32 \times 10^{-4}$ | 00.0% | 43.3 | $6.85 \times 10^{-3}$ | 0.0% |

Reactor: Thermostatted, 3/8" × 36" reactor tube.
Reactor Conditions: Pressure; 220–240 psi., [a]Reaction at 125° F., [b]Reaction at 212° F., [c]Catalyst regenerated with pure MeOH and sampled at 8 hrs. time of reaction at 150° F.; [d]Second sample at 24 hrs. time of reaction at 150° F. following regeneration, [e]Catalyst regenerated with $H_2/O_2$ treatment at 240° F. followed by reaction at 115° F.; [f]Reaction at 170° F., [g]Catalyst regenerated with $H_2/O_2$ treatment at 340° F. followed by reaction at 115° F. Liquid Flow Rate: Variable
Hydrogen Flow Rate: Variable.
Catalyst Charge: 30 mL (34.66 gms.) 54 Wt-% Zr Supported on 1/8" kieselguhr extrudates.
Feed Composition: $C_5$ feed containing approx. 0.00045 Wt-% acetonitrile (ACN) or 4.5 ppm, approx. 0.00433 Wt-% propionitrile (PN) or 43.3 ppm, 3.007 Wt-% diolefin (isoprene; 2.39 Wt-%, t-piperylene; .353 Wt-%, c-piperylene; .220 Wt-%, butadiene; .0443 Wt-%).

However, the catalyst deactivated over 8–24 hours run time. Regeneration was possible by oxidation followed by hydrogenation at 340° F. Washing with methanol allowed partial regeneration without oxidation.

Results were much better without high concentrations of dienes in the hydrocarbon feed.

EXAMPLE 2

Hydrotreatment for Nitrile Group Reduction

ACN Hydrogenation on UCI G67RS (54% Co/2.6% Zr on kieselguhr oxide) in Pure Methanol at 150° F.

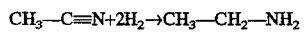

The same apparatus was used. The results and process conditions are set out in TABLE II.

TABLE II

| | ACN ppm | ACN (moles/hr.) | H$_2$ (moles/hr.) | ACN Conversion |
|---|---|---|---|---|
| FEED PRODUCT | 1100 | 2.42 × 10$^{-3}$ | — | — |
| S-#8 | 109 | 2.42 × 10$^{-3}$ | 1.875 × 10$^{-3}$ | 90.0% |
| S-#9 | 100 | 2.42 × 10$^{-3}$ | 1.875 × 10$^{-3}$ | 90.1% |
| S-#10 | 1084 | 2.42 × 10$^{-3}$ | 0.250 × 10$^{-3}$ | 1.50% |
| S-#11 | 1046 | 2.24 × 10$^{-3}$ | 0.625 × 10$^{-3}$ | 5.00% |
| S-#12 | 894 | 2.42 × 10$^{-3}$ | 1.250 × 10$^{-3}$ | 18.7% |
| S-#13 | 846 | 2.42 × 10$^{-3}$ | 1.250 × 10$^{-3}$ | 23.1% |
| S-#14 | 674 | 2.42 × 10$^{-3}$ | 1.875 × 10$^{-3}$ | 38.7% |
| S-#15 | 579 | 2.24 × 10$^{-3}$ | 2.500 × 10$^{-3}$ | 47.0% |

Reactor: Thermostatted, 3/8" × 36" reactor tube.
Reactor Conditions: Pressure; 220–240 psi., Temperature; 150° F.
Liquid Flow Rate: 3.9 LHSV.
Hydrogen Flow Rate: Variable
Catalyst Charge: 30 mL (36 gms.), 54 Wt-% Co/2.6 Wt-Zr Supported on 1/8" kieselguhr extrudates.
Feed Composition: 99.89% Methanol with 0.11% acetonitrile (ACN) by weight.
Total Operating Time: Approx. 50–75 hours.

Table II shows ACN hydrogenation on UCI G67 RS (54% Co/2.6% Zr on kieselguhr oxide) in pure methanol feedstock at 150° F. ACN conversion increases with hydrogen molar flow rate approaching 1:1 H$_2$:ACN. Activity loss is observable in S-#14. Table II indicates very high activity for the reaction of hydrogen with nitriles over a cobalt catalyst (in methanol).

EXAMPLE 3

Hydrotreatment for Nitrile Group Reduction

PN Hydrogenation on UCI G67RS (54% Co/2.6% Zr on kieselguhr oxide) in Methanol Diluted with 0.05 W % Water.

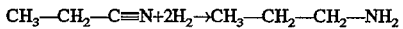

The same apparatus was used. The results and process conditions are set out in TABLE III.

TABLE III

| | PN ppm | PN (moles/hr.) | H$_2$ (moles/hr.) | Conversion | Temp., °F. |
|---|---|---|---|---|---|
| FEED PRODUCT | 146 | — | — | — | — |
| C-#40 | 11.5 | 1.871 × 10$^{-4}$ | 26.85 × 10$^{-3}$ | 92.1% | 212 |
| C-#41 | 16.3 | 1.871 × 10$^{-4}$ | 26.855 × 10$^{-3}$ | 88.8% | 212 |
| C-#42 | 3.9 | .9383 × 10$^{-4}$ | 21.42 × 10$^{-3}$ | 97.3% | 212 |
| C-#43 | 35.7 | .9383 × 10$^{-4}$ | 21.42 × 10$^{-3}$ | 75.5% | 250 |
| C-#44 | 22.6 | .9383 × 10$^{-4}$ | 21.42 × 10$^{-3}$ | 84.5% | 250 |
| C-#45 | 45.5 | .9383 × 10$^{-4}$ | 21.42 × 10$^{-3}$ | 69.2% | 250 |
| C-#46 | 2.2 | .9383 × 10$^{-4}$ | 16.065 × 10$^{-3}$ | 98.5% | 150 |
| C-#47 | 3.9 | .9383 × 10$^{-4}$ | 16.06 × 10$^{-3}$ | 97.3% | 150 |
| C-#48 | 0.0 | .9383 × 10$^{-4}$ | 16.06 × 10$^{-3}$ | 100% | 150 |
| C-#49 | 0.0 | .9383 × 10$^{-4}$ | 10.71 × 10$^{-3}$ | 100% | 150 |
| C-#50 | 0.0 | .9383 × 10$^{-4}$ | 10.71 × 10$^{-3}$ | 100% | 150 |
| C-#51 | 0.0 | .9383 × 10$^{-4}$ | 10.71 × 10$^{-3}$ | 100% | 150 |
| C-#52 | 0.0 | 1.871 × 10$^{-4}$ | 10.71 × 10$^{-3}$ | 100% | 150 |
| C-#53 | 0.0 | 2.807 × 10$^{-4}$ | 10.71 × 10$^{-3}$ | 100% | 150 |
| C-#54 | 0.0 | 2.807 × 10$^{-4}$ | 10.71 × 10$^{-3}$ | 100% | 150 |
| C-#55 | 0.0 | 4.679 × 10$^{-4}$ | 10.71 × 10$^{-3}$ | 100% | 150 |
| C-#56 | 0.0 | 4.679 × 10$^{-4}$ | 16.06 × 10$^{-3}$ | 100% | 150 |
| C-#57 | 0.0 | 4.679 × 10$^{-4}$ | 21.42 × 10$^{-3}$ | 100% | 150 |
| C-#58 | 0.0 | 4.679 × 10$^{-4}$ | 21.42 × 10$^{-3}$ | 100% | 150 |
| C-#59 | 0.0 | 1.871 × 10$^{-4}$ | 18.74 × 10$^{-3}$ | 100% | 175 |
| C-#60 | 0.0 | 2.807 × 10$^{-4}$ | 18.74 × 10$^{-3}$ | 100% | 175 |
| C-#61 | 0.0 | 4.679 × 10$^{-4}$ | 18.74 × 10$^{-3}$ | 100% | 175 |

Reactor: Thermostatted, 3/8" × 36" reactor tube.
Reactor Conditions: Pressure; 220–240 psi., Temperature; Variable °F.
Liquid Flow Rate: Variable LHSV.
Hydrogen Flow Rate: Variable
Catalyst Charge: 30 mL (36 gms.), 54 Wt-% Co/2.6 Zr Supported on 1/8" kieselguhr extrudates.
Feed Composition: 99.804% Methanol, 0.05% water with 0.146% propionitrile (PN) by weight.
Total Operating Time: Approx. 50–75 hours.

Table III shows PN hydrogenation on UCI G67 RS (54% Co/2.6% Zr on kieselguhr oxide) in pure methanol diluted with 0.05% water. Extent of reaction increased with decreasing temperature. Hydrogenation activity loss was not observable at the relatively low PN concentration in the presence of added water.

EXAMPLE 4

Hydrotreatment for Nitrile Group Reduction

PN Hydrogenation on UCI G67RS (54% Co/2.6% Zr on kieselguhr oxide) in Methanol that was Highly Diluted with Water.

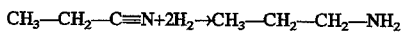
$CH_3—CH_2—C\equiv N+2H_2\rightarrow CH_3—CH_2—CH_2—NH_2$

The same apparatus was used. The results and process conditions are set out in TABLE IV.

TABLE IV

| | PN ppm | PN (moles/hr.) | $H_2$ (moles/hr.) | Conversion |
|---|---|---|---|---|
| FEED PRODUCT | 1453 | — | — | — |
| CS-#2[a] | 115 | $9.36 \times 10^{-3}$ | $16.06 \times 10^{-3}$ | 92.1% |
| CS-#3 | 89 | $6.682 \times 10^{-3}$ | $16.06 \times 10^{-3}$ | 93.9% |
| CS-#4[b] | 68 | $1.87 \times 10^{-3}$ | $16.06 \times 10^{-3}$ | 95.3% |
| CS-#5 | 81 | $3.74 \times 10^{-3}$ | $16.06 \times 10^{-3}$ | 94.4% |
| CS-#6[c] | 46 | $1.87 \times 10^{-3}$ | $16.06 \times 10^{-3}$ | 96.8% |
| CS-#7 | 104 | $9.36 \times 10^{-3}$ | $16.06 \times 10^{-3}$ | 92.8% |

Reactor: Thermostatted, 3/8" × 36" reactor tube.
Reactor Conditions: Pressure; 220–240 psi., Temperature; [a]175° F., [b]212° F., [c]150° F.
Liquid Flow Rate: Variable LHSV.
Hydrogen Flow Rate: Constant.
Catalyst Charge: 30 mL (36 gms.), 54 Wt-% Co/2.6 Wt-Zr Supported on 1/8" kieselguhr extrudates.
Feed Composition: 66.57% Water, 33.28% methanol with .1453% propionitrile (PN) by weight.
Total Operating Time: Approx. 90–115 hours (See Table III).

Table IV shows PN hydrogenation on UCI G67 RS (54% Co/2.6% Zr on kieselguhr oxide extrudates) in pure methanol that was highly diluted with water. High PN conversion of an initially very high PN concentration was accomplished at moderate temperatures in an aqueous solution. Hydrogenation catalyst activity loss was not observed. A $2H_2$:1PN or greater ratio was attained; however, complete hydrogenation was not found at any LHSV (contact time). Tables III and IV show 100 percent conversion of nitriles using methanol diluted with water as solvent. This relates to the patent or extraction of PN with methanol $H_2O$ from $C_5$'s.

EXAMPLE 5

Hydrotreatment for Nitrile Group Reduction

PN Hydrogenation on UCI G67RS (54% Co/2.6% Zr on kieselguhr oxide) in Uncontaminated, light naphta cut $C_5$ Feedstock

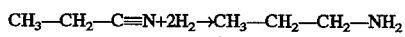
$CH_3—CH_2—C\equiv N+2H_2\rightarrow CH_3—CH_2—CH_2—NH_2$

The same apparatus was used. The results and process conditions are set out in TABLE V.

TABLE V

| | PN ppm | PN (moles/hr.) | $H_2$ (moles/hr.) | Conversion |
|---|---|---|---|---|
| FEED | 10 | — | — | — |
| DS-#1-DS-#26[a] | 0.0 | $>0.7 \times 10^{-7}$ | >0.027 | 95+% |
| FEED | 12 | — | — | — |
| DS-#27-DS-#31[b] | 0.0 | $>0.8 \times 10^{-7}$ | <0.027 | 95+% |
| DS-#32[c] | 10.9 | $>4.5 \times 10^{-7}$ | <0.027 | 9.3+% |
| DS-#33[d] | 4.26 | $>3.4 \times 10^{-7}$ | <0.027 | 64.5% |

Reactor: Thermostatted, 3/8" × 36" reactor tube.
Reactor Conditions: Pressure; 240 psi., Temperature; [1]50° F.
Liquid Flow Rate: Variable LHSV; [a,b]3, [c]17, [d]12.7.
Hydrogen Flow Rate: Excess (greater than $1.0 \times 10^{+4}/1 = 2*H_2/Nitrile$).
Catalyst Charge: 30 mL (36 gms.), 54 Wt-% Co/2.6 Wt-% Zr Supported on 1/8" kieselguhr extrudates.
Feed Composition: approx. 10 ppm; 0.0010 Wt-% propionitrile (PN) by weight, or 12 ppm; 0.0012 Wt-% propionitrile (PN) by wight, diene-free $C_5$ feed.
Total Operating Time: Approx. 1075 hours.

Table V shows PN hydrogenation on UCI G67 RS (54% Co/2.6% Zr on kieselguhr oxide extrudates) in TAME process $C_5$ feedstock. AN hydrogenation at relatively low initial AN concentration appeared to be very sensitive to LHSV (contact time). Hydrogenation catalyst activity loss was not evident.

EXAMPLE 6

Hydrotreatment for Nitrile Group Reduction

PN Hydrogenation on UCI T303 (5% Co on alumina) in light naphtha cut $C_5$ Feedstock that was Highly Contaminated with Organic Sulfur (Ethylmercaptan Poison

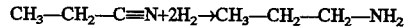
$CH_3—CH_2—C\equiv N+2H_2\rightarrow CH_3—CH_2—CH_2—NH_2$

The same apparatus was used. The results and process conditions are set out in TABLE VI.

TABLE VI

| | PN ppm | PN (moles/hr.) | $H_2$ (moles/hr.) | Conversion |
|---|---|---|---|---|
| FEED | 29.0 | — | — | — |
| DS-T1X[a] | 0.0 | $2.0 \times 10^{-7}$ | >0.027 | 99.9+% |
| DS-T2X | 0.0 | $4.9 \times 10^{-7}$ | <0.027 | 99.9+% |
| DS-T3X | 0.48 | $6.7 \times 10^{-7}$ | <0.027 | 98.3% |
| DS-T4X | 0.0 | $2.0 \times 10^{-7}$ | <0.027 | 99.9+% |
| DS-T6X | 28.91 | $5.6 \times 10^{-7}$ | <0.027 | 0.30% |
| DS-T7X[b] | 27.51 | $5.6 \times 10^{-7}$ | >0.027 | 5.10% |
| DS-T8X[c] | 0.0 | $5.6 \times 10^{-7}$ | <0.027 | 99.9+% |
| DS-T10X[d] | 14.43 | $5.6 \times 10^{-7}$ | <0.027 | 50.2% |
| DS-T11X[e] | 5.05 | $1.6 \times 10^{-7}$ | <0.027 | 82.6% |
| DS-T12X | 6.46 | $1.5 \times 10^{-7}$ | <0.027 | 77.7% |

Reactor: Thermostatted, 3/8" × 36" reactor tube.
Reactor Conditions: Pressure; 240 psi., Temperature; [a]150° F., [b]189° F., [c]340° F., [d]275° F.
Liquid Flow Rate: Variable LHSV*
Hydrogen Flow Rate: Excess (greater than $1.0 \times 10^{+4}/1 = 2*H_2Nitrile$).
Catalyst Charge: 30 mL (36 gms.), UCI T303 catalyst; 5 Wt-% Co Supported on 7–12 mesh alumina spheres.
Feed Composition: approx. 0.0029% propionitrile (PN) by weight, or 29 ppm; diene-free $C_5$ contaminated with 420 ppm organic sulfur (ethyl mercaptan source).
Total Operating Time: Approx. 510 hours. Effluent was sampled at irregular intervals with continuous, 24 hours-a-day operation. A rapid conversion loss may appear as a result of 'breakthrough' after several days reaction, i.e., between effluent analyses.

Table VI shows AN hydrogenation on UCI T303 (5% Co on alumina) in TAME Process $C_5$ feedstock. The effluent was sampled at irregular intervals with continuous, 24 hours-a-day operation. A rapid conversion loss appeared and may be a result of breakthrough' after several days reaction, i.e., between effluent analyses. Presence of sulfur compounds cause slow deactivation but recovery of activity seems possible.

The invention claimed is:

1. A process for the treatment of olefin containing hydrocarbon streams comprises feeding a hydrocarbon stream consisting essentially of a light naphtha cut containing mono olefins and minor amounts of contaminants comprising nitriles, in the presence of hydrogen and a cobalt catalyst at a temperature in the range of 30° to 200 ° C. and a pressure in the range of 50 to 300 psig to reduce the contaminants without substantial reduction of the mono olefins.

2. The process according to claim 1 wherein said material consists essentially of water.

3. The process according to claim 1 wherein said material consists essentially of methanol.

4. The process according to claim 1 wherein said material consists essentially of methanol and water.

5. The process according to claim 1 wherein said cobalt comprises 2 to 70 wt % of said catalyst.

6. The process according to claim 5 wherein said cobalt comprises about 40 to 60 wt % of said catalyst.

7. The process according to claim 5 wherein zirconium comprises about 1 to 5 wt. % of the catalyst.

8. The process according to claim 5 wherein said zirconium comprises about 2 to 3 wt. % of the catalyst.

9. The process according to claim 5 carried out at a temperature in the range of 50° to 100° C.

10. The process according to claim 1 wherein said light naphtha cut consists essentially of $C_3$ to $C_8$ hydrocarbons.

11. The process according to claim 1 wherein said naphtha cut consists essentially of $C_5$'s.

12. The process according to claim 11 carried out at an LHSV of 2 to 12.

13. The process of claim 11 wherein said cobalt and zirconium promotor is supported.

14. The process of claim 13 wherein said support comprises kieselguhr.

15. The process according to claim 13 wherein said support comprises alumina and said hydrocarbon stream is removed from said catalyst and water washed after said treatment.

16. The process according to claim 11 wherein dienes are removed prior to contact with the cobalt catalyst.

* * * * *